United States Patent
Salomon

(10) Patent No.: US 9,414,827 B2
(45) Date of Patent: Aug. 16, 2016

(54) RETRACTION SYSTEM

(75) Inventor: Dirk Salomon, Jonaswalde (DE)

(73) Assignee: IP medical Improved Performance GmbH, Dusseldorf (DE)

( * ) Notice: Subject to any disclaimer, the term of this patent is extended or adjusted under 35 U.S.C. 154(b) by 110 days.

(21) Appl. No.: 13/978,227

(22) PCT Filed: Jan. 3, 2012

(86) PCT No.: PCT/EP2012/050045
§ 371 (c)(1),
(2), (4) Date: Jul. 3, 2013

(87) PCT Pub. No.: WO2012/093114
PCT Pub. Date: Jul. 12, 2012

(65) Prior Publication Data
US 2013/0289357 A1    Oct. 31, 2013

(30) Foreign Application Priority Data
Jan. 3, 2011   (DE) .......................... 10 2011 002 412

(51) Int. Cl.
*A61B 1/32* (2006.01)
*A61B 17/02* (2006.01)
*A61B 17/00* (2006.01)

(52) U.S. Cl.
CPC .......... *A61B 17/02* (2013.01); *A61B 2017/0092* (2013.01); *A61B 2017/00858* (2013.01)

(58) Field of Classification Search
CPC ............... A61B 17/3423; A61B 17/02; A61B 2017/0225
USPC ................................................. 600/184–246
See application file for complete search history.

(56) References Cited

U.S. PATENT DOCUMENTS

| 2,493,598 | A |   | 1/1950  | Rozek |
| 2,695,607 | A |   | 11/1954 | Hipps et al. |
| 4,421,107 | A | * | 12/1983 | Estes .................. A61B 17/0293 600/206 |
| 4,430,991 | A | * | 2/1984  | Darnell ............. A61B 17/0293 600/217 |

(Continued)

FOREIGN PATENT DOCUMENTS

| CA | 1069789  | 1/1980 |
| GB | 1 520 832 | 8/1978 |

(Continued)

OTHER PUBLICATIONS

English-language translation of an Office action issued in connection with Japan Patent Application No. 2013-546733, Japan Patent Office, Oct. 28, 2015.
English-language machine translation of the abstract of Japan Patent Application Publication No. 2010-519988, Jun. 10, 2010.

*Primary Examiner* — Ellen C Hammond
*Assistant Examiner* — Christina Negrellirodrigue
(74) *Attorney, Agent, or Firm* — DASCENZO Intellectual Property Law, P.C.

(57) ABSTRACT

The invention relates to a retraction system for exposing accesses in human medicine, dentistry or veterinary medicine, wherein said retraction system is arranged on the respective body region and has at least one hook-shaped retractor element 1 and retaining means for fixing the latter. The retraction system is characterized in that it is made of a radioparent material and in that it has a self-retaining action and/or is flexible at least in some areas such that, during retraction, a flexible element or a flexible section nestles against a tissue that is to be retracted.

34 Claims, 11 Drawing Sheets

(56) References Cited

U.S. PATENT DOCUMENTS

Figure 1:
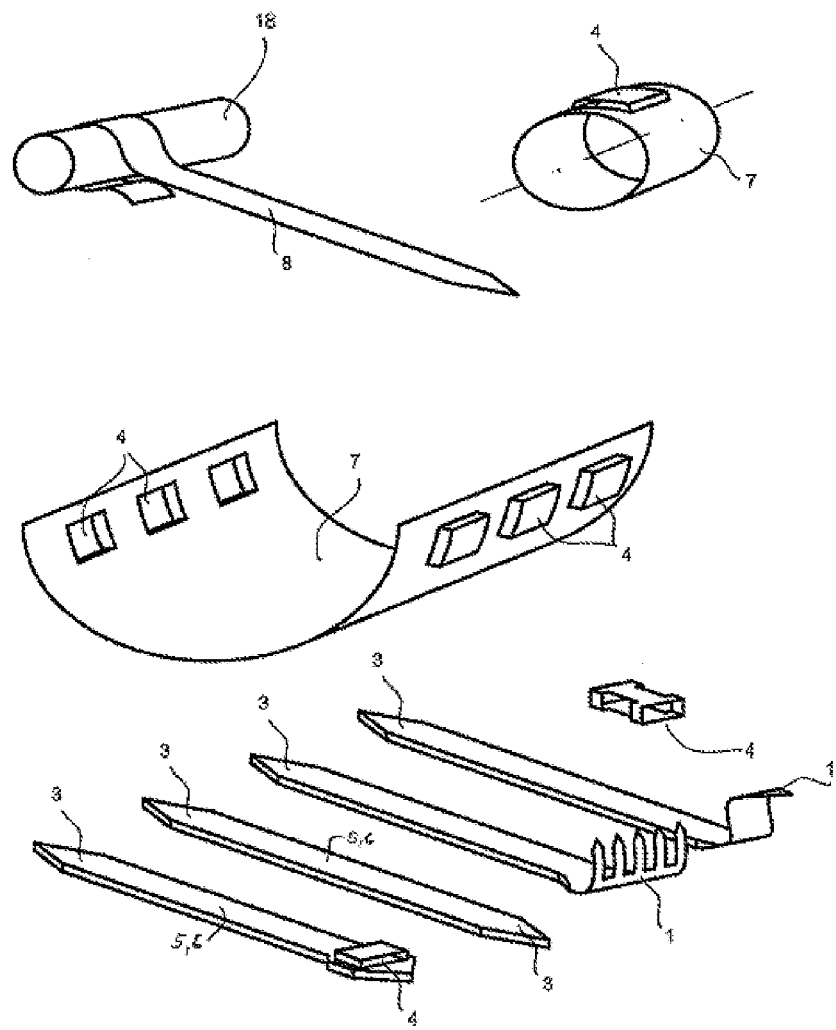

| | | | |
|---|---|---|---|
| 5,307,790 A * | 5/1994 | Byrne | A61B 17/02 240/20 R |
| 6,117,072 A | 9/2000 | Fowler, Jr. | |
| 6,824,511 B1 | 11/2004 | Bell et al. | |
| 2005/0080320 A1* | 4/2005 | Lee | A61B 17/02 600/214 |
| 2008/0021286 A1 | 1/2008 | Risto et al. | |
| 2010/0030260 A1 | 2/2010 | Fleischmann | |

FOREIGN PATENT DOCUMENTS

| | | |
|---|---|---|
| JP | 51-109187 | 9/1976 |
| JP | 2008-525150 | 7/2008 |
| JP | 2010-519988 | 6/2010 |
| WO | WO 94/06354 | 3/1994 |
| WO | 2006/071188 | 7/2006 |

* cited by examiner

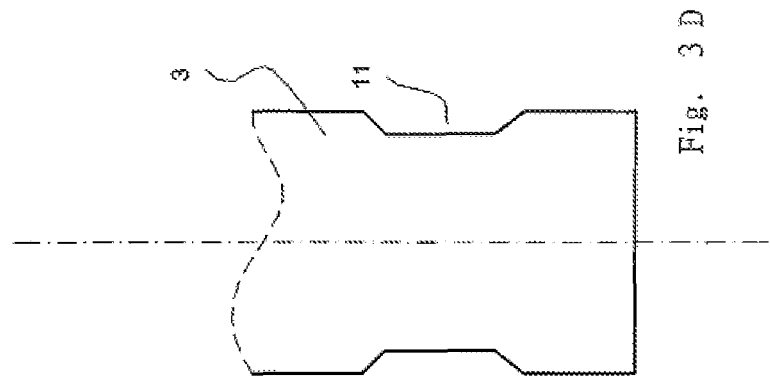
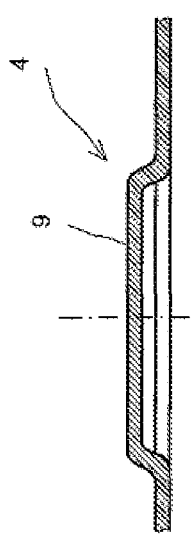
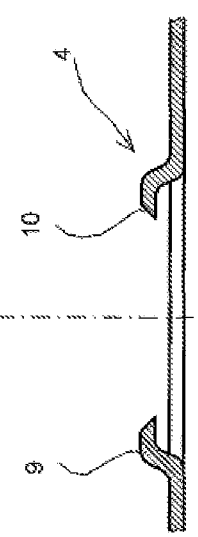
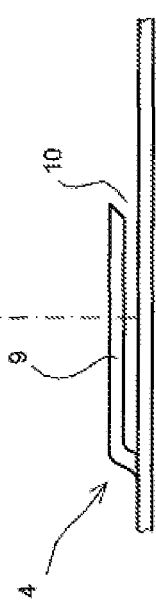

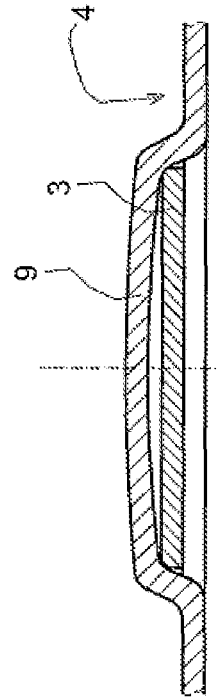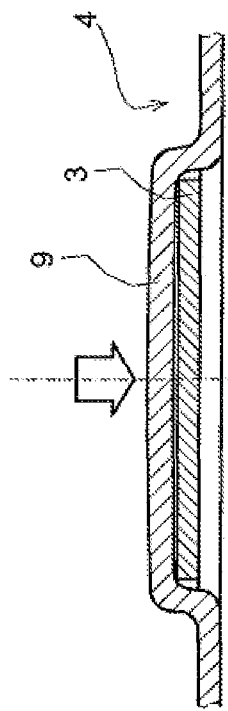

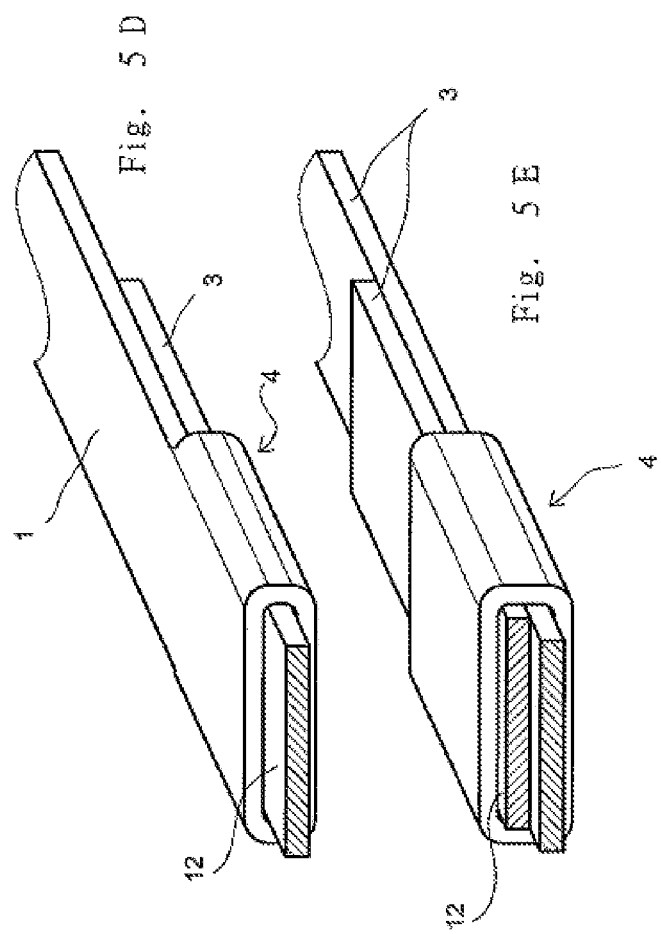

RETRACTION SYSTEM

In general, the invention relates to a retraction system for exposing accesses in human medicine, veterinary medicine or dentistry.

In order to keep surgical accesses open, use is made of various retraction instruments, in which retractor elements, e.g. retractors, are inserted into the incision in order to create a surgical access by tensile force. By way of example, Hohmann retractors, which pull apart the opposite sides of the opened-up access, are known as retractor elements. The main problem here lies in ensuring the continuous fixation of the patient to a sufficient extent. To this end, at least one assistant is required, who pulls the opening apart by means of the Hohmann retractors.

A further problem emerging during lengthy interventions is that, with increasing duration, the risk of inadvertent movements by the assistant increases, which in turn requires renewed fixation or could possibly also have effects on the course of the operation. A further significant disadvantage moreover emerges from the fact that the operator finds the access to the operation field and view and illumination to be restricted, which causes significant disruption to the operation progress.

It is for this reason that various holding systems, which, in part, are complicated to put on and which form a retraction system in conjunction with the retractor elements, are already known. Very complex retraction systems, in which the retractor elements are held and fixed by means of various rods, are known.

However, it is not possible to use these in every case and they sometimes inadvertently restrict the operation field.

WO 94/06354 A1 describes a retraction system for limbs, which consists of two tapes which each have a hook for retraction at one of their ends. Here, the two tapes encompass the body limb in such a way that in each case one tape is guided around the body limb in a circular fashion, starting at the incision. On the underside of the body limb, the two tapes engage with one another by means of a clamping device. This brings about tensile force acting in the circular direction, which spreads the opened-up tissue, wherein there is a stepwise adjustment of the tensile force by means of the clamping device.

A disadvantage of the above-described retraction systems consists in the fact that the use of metallic materials makes the use of intraoperative x-rays significantly more difficult, which is undesirable, particularly in the operation region.

Furthermore, the above-described retractors have to be removed during the operation and reinserted, for example in order to enable intraoperative x-ray imaging or movement manipulations on the body limb. Thereafter, renewed fixation is required on a regular basis. This firstly increases the operation times and also increases the risk of infection for the patient. Moreover, the tissue can also be damaged during repeated insertion.

Moreover, the known systems have to be subjected to a cleaning and sterilization process after use in order to be able to be used for a further operation. As a result of this, there also is a residual risk of infection when using such systems since possible problems can occur at this stage. Moreover, a problem of systems with a complicated design lies in sterilizing the whole system, said sterilization being problematic on account of the shape and also, often, on account of the size.

The object of the present invention therefore lies in specifying a retraction system which can be used in adaptable fashion for very different operation fields and which overcomes the above-described disadvantages.

The object is achieved by a retraction system in accordance with the main claim. Advantageous embodiments are specified in the dependent claims.

According to the invention, a retraction system arranged on the respective body section is proposed, which retraction system comprises at least one hook-shaped retractor element and holding means for fixing it on the body section, which retraction system is made of a material transparent to x-rays and embodied to be self-retaining or flexible, at least in sections, or has both of the last-mentioned properties. The flexibility is such that a flexible element or a flexible section nestles against tissue to be retracted during the retraction.

The proposed retraction system permits, both in conjunction with the self-retaining fixation on the patient and with the flexible property, the use of materials transparent to x-rays such that x-ray examinations can be carried out during an operation. The fixation of the operation field provided by the retraction system according to the invention can continue during the x-ray during the operation, which is why a re-fixation, which is required otherwise, can be dispensed with.

Here, self-retaining should be understood to mean that the stabilization of the implemented retraction system and the holding forces currently having to be applied for the retraction are realized without external intervention and this in situ on the body in accordance with the general conditions and the subjectively specific conditions for the application region. The forces absorbed by the retraction system are sufficiently large to take on the tensile forces required for the retraction and to inherently stabilize the system. Accordingly, such an independently acting retraction system can be adapted both to the requirements of the various body types and to the special body conditions of a patient as well as to the surgical requirements. Moreover, the attachment on the body part to be treated can take place adapted to the anatomical conditions in situ.

The self-retaining functionality permits a freedom of movement of the body part which is restricted by the body part and the operation conditions but not restricted, or only restricted to a small extent, by the retraction system, such that e.g. mobility tests can take place in the retraction state.

The anatomical adaptation to the respective body part and the dimensions thereof, such that the retraction system is self-retaining, can occur in various ways. In many cases, the body part can be encompassed in a circular fashion, wherein the holding forces, which are applied by the system itself, can also be strengthened on account of a radial force component emerging from the circular wraparound. Additionally, in accordance with special embodiments, connections to adjacent body parts are also possible. Moreover, the retraction system also permits links to external structures in order to obtain an interaction in these cases in which the type of intervention requires this.

In addition to the self-retaining property, or as an alternative thereto, the retraction system is, at least in sections, embodied to be flexible; to be precise, in such a way that at least the relevant retractor element and, depending on the functional element used, the parts thereof as well nestle against tissue to be retracted during the retraction. The combination of the material transparent to x-rays and the self-retaining and/or flexible properties improves the handling, even during the course of the operation, by virtue of the retraction system being associated more with the body part than the existing systems.

As a result of a suitable shape of the relevant elements and sections, these can be employed in situ, nestling against the operation field and the anatomical conditions themselves. In conjunction with the use of material transparent to x-rays, the flexible properties can be adapted very flexibly to the respective application and the force situation connected therewith. This can be brought about by the selection of the material and/or the shape of the element or section, such that the desired nestling in the operation field and a self-optimizing retraction for different operation fields, e.g. in respect of the size and the tissue to be spread, and patients, e.g. stocky and less stocky, can be obtained.

The flexible, nestling property of said elements moreover brings about improved opening-up of the operation field compared to the known, rigid retractors. In addition to spreading the tissue, yielding and nestling elements simultaneously hold down the surrounding tissue. Depending on the use of retractor elements, it is moreover also possible to position and/or fix body parts better in the operation field, e.g. lift bones. As a result, the access for the operator can be significantly improved.

The nestling property and the adaptability of the retraction system to the respective situation moreover bring about the possibility of avoiding tissue being stressed. As a result of the flexible elements imparting loads that act on the tissue, it is possible, for example, to prevent bruises or strains.

In accordance with one embodiment, the retraction system is designed in modular fashion from different elements that can be combined with one another in very different ways. It comprises functional elements, which can be combined with one another in very different ways and thus permit adaptations to the operation field for very different body parts and adopt the necessary retraction. It moreover comprises lock elements and closing elements, which realize the connection between the functional elements amongst themselves in a self-retaining fashion. To this end, each functional element has at least one lock element or closing element. This basic system of functional elements and lock elements and closing elements, of which each functional element has at least one, permits a minimization of the individual parts in the case of the greatest possible variability of the system in accordance with the greatly varying anatomical conditions.

It follows that the essential elements of a retraction system are retractor elements as basic functional elements, which ensure the access being opened up, and lock elements and closing elements, wherein a closing element should denote the counterpiece to the lock element, which closing element engages directly into the lock. At least the lock elements, but possibly also both types, are configured in a self-retaining fashion and enable a force-fit connection of very different elements of the overall system amongst themselves, e.g. of the retractor elements amongst themselves or with other elements.

As illustrated in more detail in the exemplary embodiment below, connecting retractor elements with lock elements or closing elements leads to there being adjustability when assembling a retractor element in the effective direction thereof, i.e. in the retraction direction. This significantly improves the possibility of setting the retraction in situ and in accordance with the anatomical conditions, particularly in conjunction with a modular assembled retraction system.

Supported by the modular system, hooks which are designed in terms of the shape and effectiveness for specific applications can also be used as retractor elements in addition to the usual conventional retractors such as Hohmann-like hooks, Langenbeck-like hooks in all lengths and widths, sharp, pointed, blunt hooks and Roux hooks. By way of example, the retractor elements can also be equipped with illumination aids.

Further functional elements of the overall system with a modular design can include:

extension elements which, if required, enable a more comprehensive length adaptation of the retraction system during the operation, cross-connection elements which are employed for stabilizing and fixing the position between adjacently arranged functional elements, in particular between adjacent retractor elements, compensation elements which enable an angular compensation or length compensation in the case of a non-symmetrical opening of the access, specific shape elements which, as functional elements adapted to the anatomy, enable an adaptation of the retraction system to the anatomical conditions in the region of the access, and adaptation elements which ensure a combination with other instruments and devices.

Further functional elements can be integrated. For realizing various functions, the functional elements can be combined with one another by means of the integrated and/or separate lock elements and closing elements.

Thus, cross-connection elements, which are employed for stabilizing and fixing the position between adjacently arranged retractors, have lock elements and/or closing elements in different possible combinations, as described above in respect of the extension elements. This is particularly advantageous in order to ensure a coordinated retraction with common pulling direction between adjacent retractors.

Compensation elements are used to achieve an optimum geometric adaptation of the whole system or individual components in terms of angle, for example when employing the retraction system in the region of the joint, and length, for example by means of elastic functional elements. This ensures an optimum adaptation of the retraction system to the operation region, enabling an improved retraction effect while having a reduced load on the patient. The connection thereof to adjoining functional elements of the retraction system can also be brought about via lock element and closing element.

Specific shape elements adapted to the anatomy or the access are used for additionally supporting the above-described retraction systems. Here, provision is made for shell-like functional elements, such as a wrist support, or else separate holding elements, such as e.g. devices that are pushed onto the finger. This is particularly advantageous to bring about a fixation of adjoining limbs or to integrate these into the holding device of the retraction system. To the extent that the design of the shape elements permits this, the connection thereof to adjoining functional elements of the retraction system via lock elements and closing elements can alternatively also be brought about under the insertion of e.g. a compensation element or an extension element.

As mentioned above, provision is made for adaptation elements, with the aid of which the retraction system is employed to hold or guide other instruments, such as devices for removal by suction, endoscopic instruments, probes, infusion tubes, x-ray markings, optical units, illumination means, navigation aids, guides or gauges or other equipment, or coupled to other fixation systems. Here, the retraction system according to the invention is employed by means of adaptation elements in order to act as a holding device for further instruments. This renders it possible to ensure targeted guidance of the instruments in the operation region, which ultimately enables improved accessibility of the opened-up operation region. The adaptation elements can also optionally be connected to the system via lock elements and closing elements.

A further advantage of the modular retraction system emerges by virtue of the fact that, in contrast to known systems, it is possible to separate sterile from non-sterile elements, since only those elements of the system which are in contact with the operation field are to be kept sterile. This will regularly be at least the retractor elements. Other elements, such as e.g. adaptation or extension elements and the associated or assigned lock elements and closing elements, may lie in the non-sterile region. A separation between sterile and non-sterile elements can be selected more or less freely in accordance with the operation region. Hence, completing the system can flexibly be adapted to the requirements both in terms of time and in respect of the sterility and a possible link to further operation equipment.

Provided that closing elements, lock elements or various functional elements have a flexible design, this moreover results in improved connection options for the various elements during the operation, which is advantageous, particularly for a modular retraction system.

In a further embodiment of the invention, the above-described flexible elements or element sections have an elastic design. The elastic properties of one or more elements or sections thereof lead to said elements and sections returning to their original shape after the load was removed and being able to have pretension, which supports the forces required for the retraction and also the self-retaining system. What is more, a pretension of an elastic element can be employed to improve further the adaptation to the force situation in the operation field and hence the accessibility to the exposed body parts, as explained above.

Which elements should have the flexible or optionally elastic properties depends substantially on the operation field. Depending on which of the aforementioned effects which are also possible in addition to spreading should be obtained, this may either be only one or more retractor elements or one or more functional elements or sections thereof, or else various combinations thereof. If the retractor elements are flexible or elastic, shapes which are well adapted to the force situation in relation to the tissues and the bones emerge during the application thereof. Hook and/or lever shapes, which obtain improved retraction effects, emerge. In the case of a retraction system with a modular design, the adaptation of the retraction system to the given situation can be undertaken at that time.

In a further embodiment of the invention, functional elements of the retraction system, in particular the retractor elements, have tape-like ends, which serve as a closing element and are connected by force fit by a self-retaining lock part.

In conjunction with the lock elements, the tape-like ends permit simple handling under operation conditions, various combination options to lock elements and moreover structurally simple designs, which also enable simplifications in respect of the sterilization. Moreover, the tape-shaped ends in accordance with one embodiment of the invention permit the continuously adjustable setting of the length over a freely selectable, large region. By way of example, the continuously adjustable setting can be achieved by clamping the tape in the lock element.

As described above, the lock elements and closing elements are designed to be self-retaining, wherein various designs, described in more detail below, are possible. The subsequent descriptions of lock elements with web-like clamping elements, which clamp the inserted closing elements, should merely in an exemplary fashion depict such force-fit connections between lock elements and closing elements, by means of which a continuously adjustable adjustment of the two functional elements with respect to one another is ensured.

In a further embodiment of the invention, lock elements and/or closing elements are separate parts for coupling a plurality of other functional elements. In particular, this is advantageous to ensure a flexible design of the retraction system in accordance with the anatomical conditions in the operation region.

In order to simplify the positioning of the connection between functional elements or to prepare said positioning of the connection for quick completion during the operation, a closing element can have a positioning means, by means of which a separate lock element can be positioned.

Alternatively, or in addition thereto, lock elements and/or closing elements are connected to retractor elements in a functionally integral fashion or integrated into other functional elements such that a retractor element or another functional element can have different numbers and arrangements of lock elements and/or closing elements. This is advantageous in order to ensure fast fixing and releasing of the various elements. Thus, it is also possible to use elements with functionally secure or else routinely integrated lock elements and/or closing elements during such interventions, where the anatomical conditions of the operation region only exhibit small deviations.

By way of example, extension elements, which generally have a tape-like design, can have one or two lock elements or closing elements. The combination of one or more lock elements and closing elements on one extension element is also possible. Here, the lock elements and closing elements are designed and combined with one another in such a way that extension elements for all of the aforementioned functional elements of the retraction system are available. The extension elements are advantageously used particularly in the case of very obese patients.

As a result of the various combination options for the functional elements, it is advantageous if, in one embodiment of the retraction system, lock elements are able to hold two or more closing elements. As a result, several functional elements can coincide at one point and the element number can be optimized without restricting the functionality. Thus, there can also be angled connections, corresponding to the anatomical conditions, in an angular range between 0 and 180° between the lock element and a closing element or two or more closing elements coinciding in the lock element.

In order, depending on the design of the closing elements, to enable a simple and quick connection to a lock element, the lock elements can have different connecting means in different embodiments. Thus, means for inserting the closing element are possible, as a result of which is easily possible to set the length over a large range via the depth of the insertion of a tape-shaped closing element. It is also possible to prepare the connection by virtue of the closing element initially being inserted in a loose manner and only being finally connected after the final positioning of the functional element to be held.

Means for laying-in are also possible, which permit firstly to position the functional element correctly and then to fix it without requiring displacement. In this or in other types of connection, having the closing element snapping into a pre-position or final position can be helpful in order to signal the positioning or fixing acoustically by a snapping noise.

It is advantageous in the aforementioned connection options if at least one closing element consists of an elastic material. Moreover, particularly for an anatomical adaptation of the functional elements, it can be advantageous if the closing elements, and optionally lock elements as well, are also elastically deformable.

In a further embodiment, the surface of the material transparent to x-rays has, at least in those sections in which the elements of the retraction system, i.e. the lock elements and closing elements and functional elements, are connected, microstructuring, which amplifies the self-retaining effect of the retraction system. The microstructuring of the surface of the material transparent to x-rays should be understood as an increased surface roughness, which leads to an improvement in the holding effect of the retraction system.

Depending on the material used, the structures can be caused by the material itself, e.g. if structured tissues are used, or can be produced by processing or coating the surfaces of the relevant sections. Alternatively, the production process of the elements, e.g. the shaping thereof, can also be designed in such a way that the completed elements have the desired surface structure.

In order to support the continuously adjustable option for setting, the surface structures have dimensions in the region of at most 2 mm, preferably in the range from 0.1 mm to 1 mm and can be designed regularly, e.g. as surface texture, or stochastically.

Further advantages emerge from the use of x-ray beam-transmissive material. By way of example, if a high temperature resistant, thermoplastic polymer such as e.g. the high-performance polymer polyether ether ketone (PEEK) or PE is used, it can, in addition to thermal and mechanical solidity, also have the aforementioned elastic deformability for self-adaptation of the elements to anatomical conditions.

A further advantage of using polymers consists in the option of designing the retraction system, or at least, however, the elements to be kept sterile, as disposable elements. This dispenses with the otherwise necessary sterilization before the operation begins, which in turn leads to a reduction in the time spent preparing the operation, since these parts can already be sterilized and packaged after production.

Figure 2A:
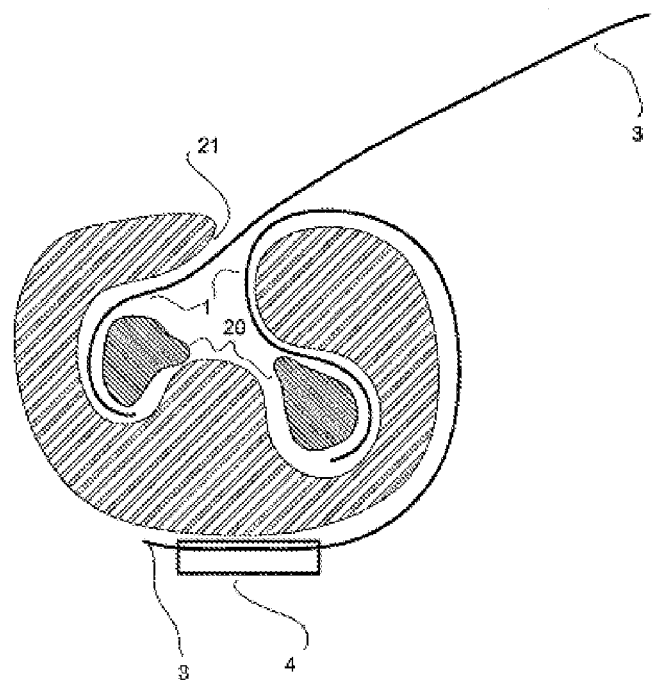
Figure 2B:
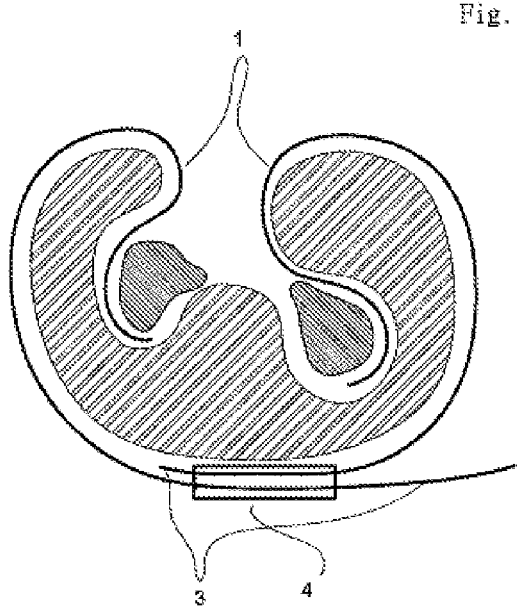
Figure 3:
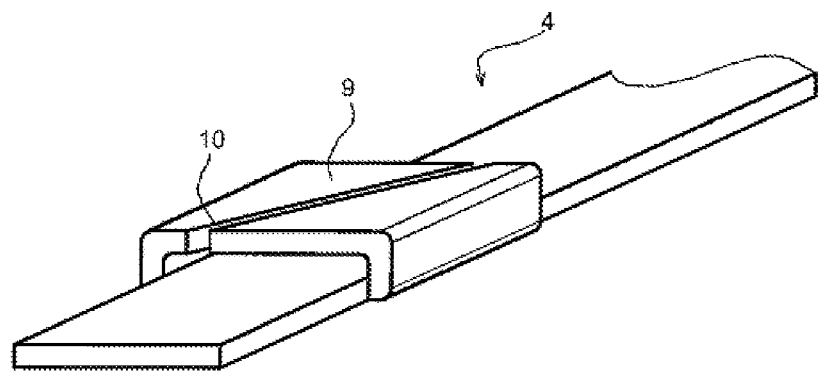
Figure 5A:
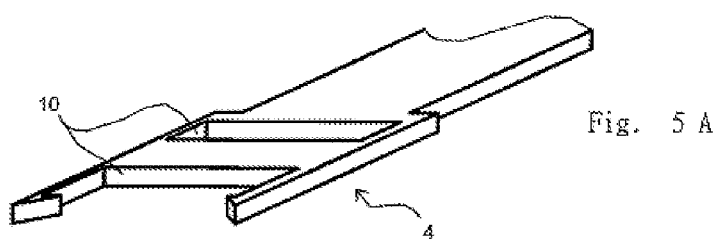
Figure 5B:
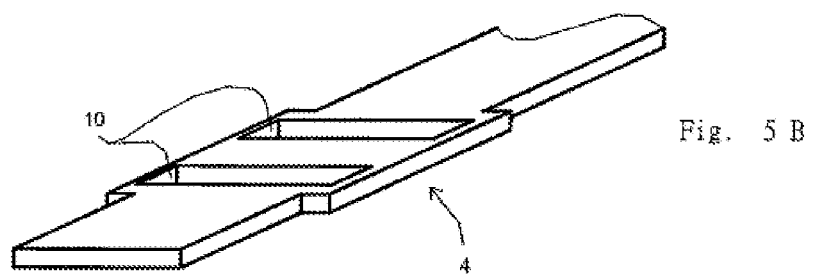
Figure 5C:
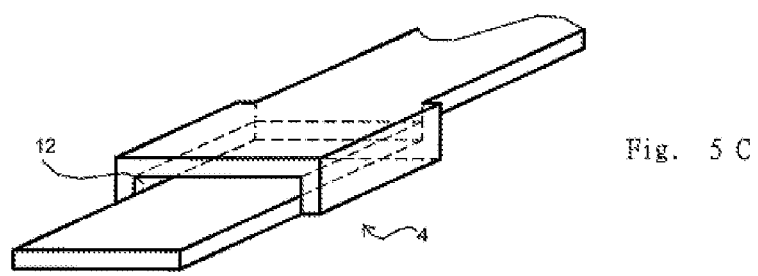
Figure 6:
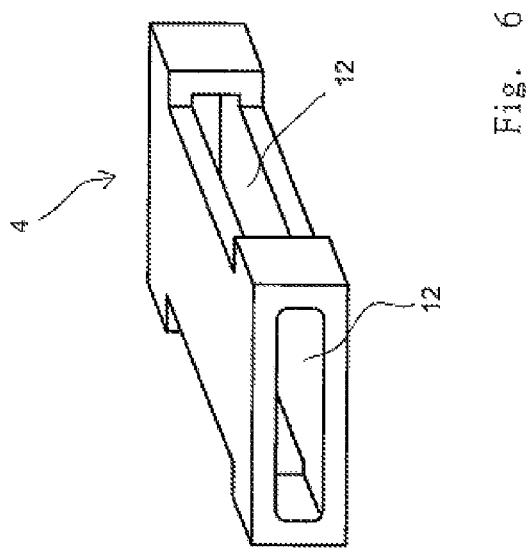
Figure 7:
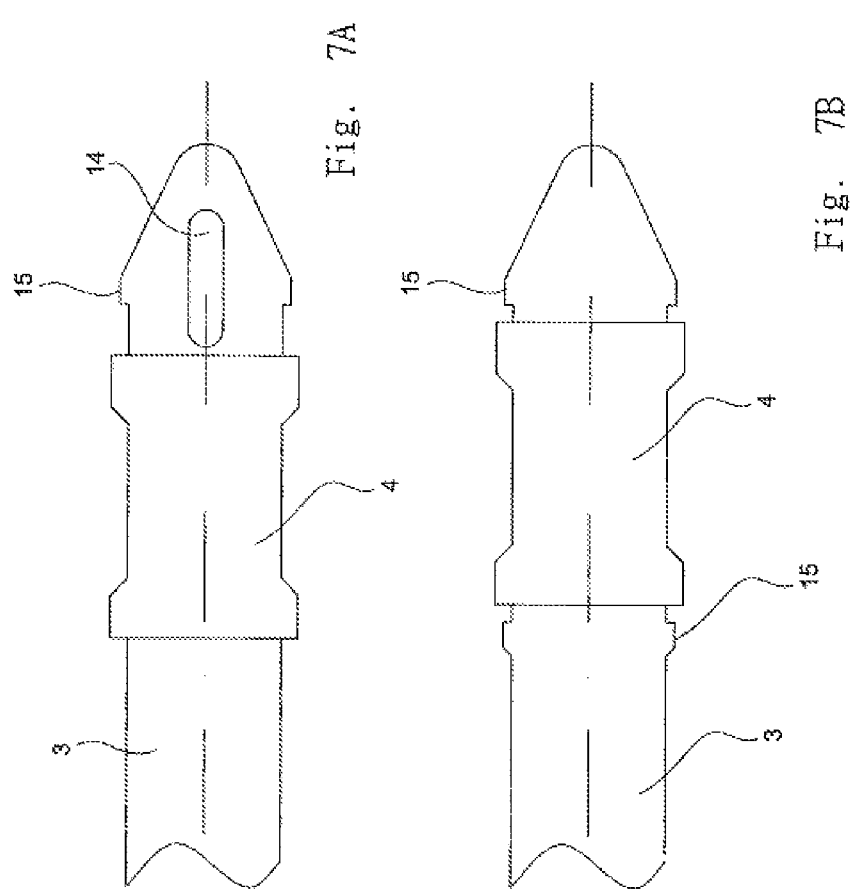
Figure 8:
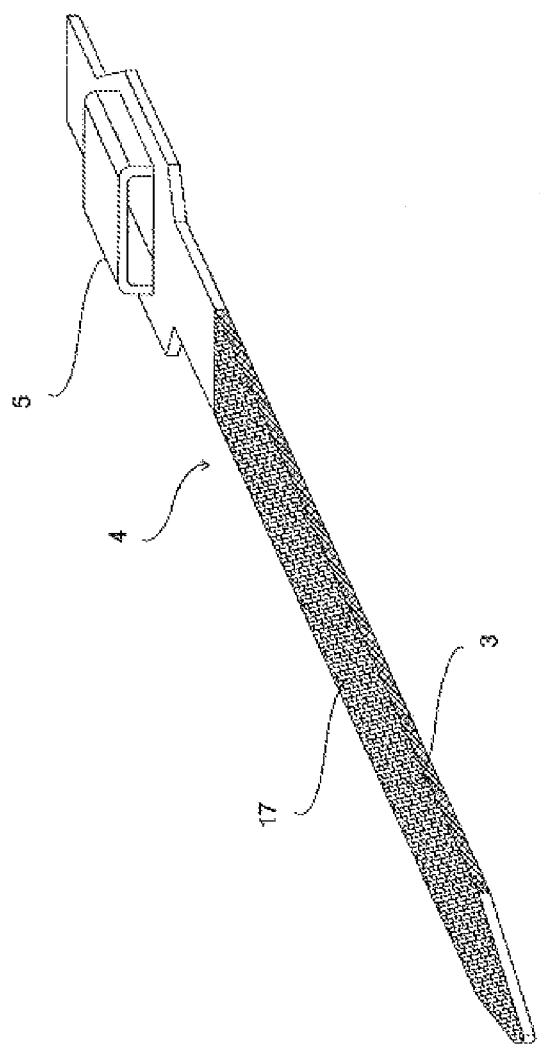
Figure 9:
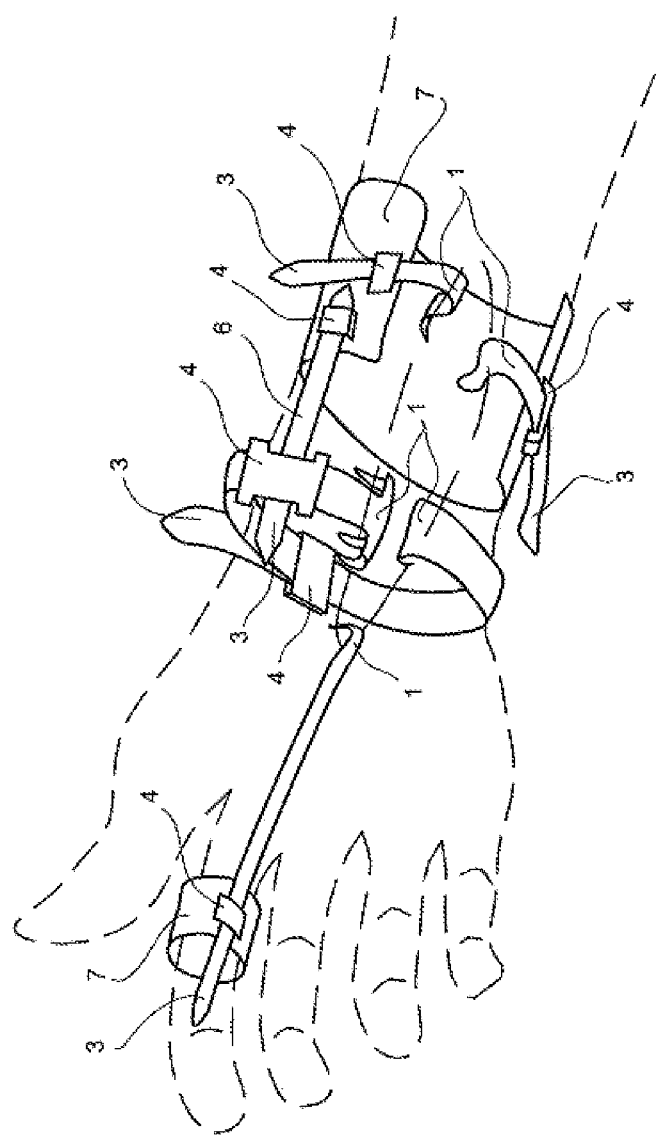

In the following text, the invention should be explained in more detail on the basis of figures and exemplary embodiments. In detail:

FIG. 1 shows a schematic illustration of individual components of a retraction system according to the invention, FIGS. 2A and 2B show an embodiment of a retraction system with elastic elements in two different employment states on one limb (sectional illustration), FIGS. 3A to 3E show embodiments of lock elements and closing elements, FIGS. 4A, 4B show sectional illustrations of lock elements with closing elements, FIGS. 5A to 5E show embodiments of lock elements, which are integrated into functional elements, FIG. 6 shows an embodiment of a lock element with a crossed plug, FIGS. 7A, 7B show a schematic illustration of embodiments of closing elements that can snap in, at a tape-like end, FIG. 8 shows a lock element with closing element with microstructuring on the surface of the closing element, and FIG. 9 shows a schematic illustration of an exemplary retraction system according to the invention for the hand region.

FIG. 1 initially illustrates individual components of the retraction system in an exemplary fashion.

In order to retract the surgical access, use is made of retractor elements 1, the shape of which is adapted to the requirements in the operation field. Here, retractor elements 1, such as Hohmann-like hooks, Langenbeck-like hooks in all lengths and widths, sharp, pointed, blunt hooks, Roux hooks and also hooks and other shapes, can be used which are designed in terms of their shape and effectiveness for specific applications. In the illustrated embodiments, the retractor elements 1 are, in an exemplary fashion, respectively connected to a closing element 3 by virtue of being arranged at one end of a tape-shaped element. The other ends of the tape serve as closing elements 3. Separate retractor elements 1, which can be connected to one of the further functional elements in a suitable manner, are also possible.

The retraction system furthermore comprises lock elements 4, which are either arranged at one end of a tape-shaped functional element or, as illustrated in FIG. 1, embodied as a separate element. The lock elements 4 are embodied in an auto-clamping manner and serve for a force-fit connection to the closing elements 3. Incidentally, as described in detail below, the closing elements 3 are inserted, e.g. plugged-in, into the lock element 4, as a result of which the auto-clamping effect of the lock elements 4 emerges. A continuously adjustable retraction is possible by inserting the closing elements 3, which are arranged at the end of the retractor elements 1, into the lock elements 4. By way of example, when encompassing a body element in a circular fashion, there usually is, depending on the size thereof, a radial force component, which amplifies the clamping effect in the lateral direction, from the closing element 3 onto the lock element 4.

The retraction system illustrated in FIG. 1 furthermore comprises extension elements 5, which preferably have a tape-shaped design. The extension elements 5 are advantageous particularly when using the retraction system on limbs or body regions with increased circumference, which cannot be encompassed by the tapes arranged on the retractor elements 1. Here, the extension elements 5 can likewise have lock elements 4 and closing elements 3 in order to ensure an auto-clamping connection between the individual elements, which in turn enables the tensile force for the retraction by simple setting of the continuously adjustable connection. The extension element 5 in accordance with FIG. 1 has two closing elements 3 in the form of tape-shaped ends.

For the further stabilization of a retraction system, provision is furthermore made for cross-connection elements 6, which enable a connection between the individual retractor elements 1 and hence lead to an improved fixation of the retractor elements 1. The cross-connection elements 6, comparable to the extension elements 5, are preferably designed in a tape-shaped manner. In FIG. 1, the cross-connection elements 6 and extension elements 5 are equipped with the various possible lock elements and closing elements 3, 4. They are embodied as a tape and have a tape-shaped closing element 3 at one end and a lock element 4 at the other end, or have closing elements 3 at both ends. FIG. 1 furthermore shows a possible shape of a separate lock element 4. It will be illustrated in FIG. 5 and described in more detail.

In addition to the elements described above, the retraction system furthermore comprises specific shape elements 7, which are adapted to the anatomy or the access. These shape elements 7 are arranged on a limb, etc. in accordance with the anatomical conditions present. By way of example, a shape element 7 can be embodied as a functional element to be plugged onto a finger, as illustrated in FIG. 1. Or it is shaped from a relatively large plate that can be designed in various ways, to be applied on extensive body parts, such as a limb or the back. In any case, a shape element 7 also comprises a closing element or a lock element 3, 4, which renders possible the holding of an additional retractor element 1 or the connection to a further functional element. Alternatively, it is also possible to arrange other functional elements, which comprise a closing element 3, on the specific anatomical shape element 7, such as illumination means etc.

The retraction system furthermore comprises adaptation elements 8, which are used for holding and guiding other instruments, such as probes, devices for removal by suction, endoscopic instruments, etc. Alternatively, the adaptation elements 8 for the connection to other fixation systems can be provided as an external system 18, i.e. not belonging to the retraction system. As a result of using adaptation elements 8, an extended modular design of the retraction system and hence a specific adaptation to the requirements of the operator is possible. As a result of the fact that each one of the functional elements has at least one lock element 4 or one closing element 3, the various functional elements in accordance with FIG. 1 can be interconnected in very different combinations.

FIG. 2A depicts a schematic illustration of a retraction system according to the invention in an exemplary fashion. Here, there is a retraction of the surgical access by means of two retractor elements 1, the shape of which at one end of each tape-shaped retractor element 1 is styled on the known hook shapes. The retractor elements 1 and the tape-shaped extensions adjoining these have an elastic design up to the closing elements 3, wherein the pre-bent, hook-shaped ends of the retractor elements 1 have such an elasticity that permits greater forces to be absorbed while maintaining their shape. To the extent that this is required, they can also have a rigid design. In addition to the elastic retractor with closing elements 1, 3, the illustrated retraction system comprises a separate lock element 4, into which the two closing elements 3 can be inserted in opposite directions.

The connections between the individual retractor elements 1 of the retraction systems is brought about as described above by means of the lock element 4 and the closing elements 3. As an alternative to the illustrated embodiment, these can also be present combined with one another on a retractor element 1. The various designs illustrated in FIG. 3 to FIG. 8 and described below in more detail can be used for this.

FIG. 2A illustrates the retraction system during the positioning thereof, wherein one of the two closing elements 3 is already connected to the lock element 4. The tape-shaped extension of the right-hand retractor element 1 in FIG. 2A, which has a closing element 3 at its free end, in this case encompasses half a circumference of a limb to be operated upon such that the closing element 3 engages into the lock element 4. By inserting the closing element 3 into the lock element 4, there is an auto-clamping connection between lock element and closing element 3, 4.

The left-hand retraction element 1 is likewise positioned under the bone 20. However, the closing element 3 thereof has not yet been connected to the lock element 4, and so only the pre-shaped end thereof has a shape similar to that of the final usage state. The tape-shaped extension does not yet encompass the tissue 21 in the illustrated state, and so its shaping effect on the tissue compared to the right-hand, utilized element becomes visible.

As a result of the elasticity of the pre-shaped free ends of the retractor elements 1, these can easily be inserted under the bones 20. The elasticity of the remaining sections permits a simple connection to the lock element 4.

In FIG. 2B, the closing element 3 of the left-hand retractor with functional element 1, having the same design as the right-hand one, is also connected to the lock element 4, and so the two closing elements 3 overlap. The retraction now takes place by means of continuously adjustable adaptation of the tensile force of the retractor elements 1 by changing the length of the closing elements 3 in the lock elements 4. The correspondence between setting direction and retraction direction can be identified on the basis of this example. During the retraction, the elastic tape-like parts of the functional elements nestle against the tissue shape and slightly reshape it, compensating the forces.

As a result of the elasticity of the free ends of the retractor elements 1, when the latter are inserted under the exposed bones 20, a lever action is exerted onto the bones 20 by the tissue 21, which lies thereover and is encompassed by the functional element, such that the bones 20 are slightly lifted in the direction of the opening (not illustrated). At the same time, the surrounding tissue 21 is spread by the retractor elements 1 nestling against the bone 20 and tissue 21, held aside and slightly pressed down in the process. As a result, the elastic retractor elements 1 enable good access to e.g. the bone 20.

The following embodiments depict various lock elements and closing elements 3, 4 which can be used for a modular retraction system. In one embodiment in accordance with FIG. 3A, a lock element 4 has a web-like clamping element 9 in that region which, when used, preferably lies on the side of the lock element 4 facing away from the body; this is referred to as the upper region below. A matching closing element 3, e.g. a tape-like end of another functional element (not illustrated), can be inserted into the clamping element 9 such that it is held by a force fit.

As an alternative, the web-like clamping element 9 can be cutout in sections in a lock element 4 such that a closing element 3 (not illustrated) can be snapped in. FIG. 3B shows a cutout 10 on the longitudinal side of the web of the clamping element 9.

In a further embodiment of a lock element 4, the web-like clamping element 9 has a lateral cutout 10 (FIG. 3C), through which a closing element 3 (not illustrated) can be inserted and latched and held in its position by the forces acting thereon during use.

The insertion of the closing element 3 into a cutout 10 of the web-like clamping element 9 can be assisted by a matching shape of the closing element 3. FIG. 3D illustrates, in an exemplary fashion, a thinned section 11 of the tape-like closing element 3. After it has been inserted through the cutout 10, the closing element 3 can be displaced up to the correct position and affixed there.

In a further embodiment of a lock element 4, the web-like clamping element 9 has an oblique cutout 10 (FIG. 3E), through which a closing element 3 (not illustrated) can be inserted, optionally displaced for setting the length, and held in its position by the forces acting thereon during use.

An alternative embodiment of the lock elements 4 as clamping elements 9 permits a simple opening of the connection between lock element 4 and closing element 3, as illustrated in FIG. 4A. By virtue of a force being exerted on the web of the clamping element 9—illustrated in FIG. 4B by arrows in the effective direction thereof—the passage formed through the web widens, and so the lateral edges of the closing element 3, e.g. a tape-shaped end of a retractor element 1, are released (FIG. 4B). In this position, it is possible to displace the closing element 3 and, by terminating the force action, clamp it tight again. Such functionality can easily be applied and is supported, in particular, by producing the elements from plastic, tissue or the like as integral components, which can easily be sterilized and are economical in production.

FIG. 5A to FIG. 5E show various embodiments of the lock element 4, which are arranged on one of the functional elements, as a result of which a connection to other functional elements, which connection can be continuously adjustably set, can be established by inserting the closing elements 3 thereof.

The embodiments in accordance with FIGS. 5A and 5B are embodied comparable to a buckle and are suitable for elastically deformable tape-shaped closing elements 3 (not illustrated). While the lock element is arranged at the end of a functional element, which is tape-shaped at least in this section, in the embodiment according to FIG. 5A, in FIG. 5B it is situated in the central section of a functional element which is tape-shaped at least in sections. A likewise tape-shaped closing element 3 is held by the two cutouts 10 which are arranged next to one another.

The lock element 4 in accordance with FIG. 5C is formed by a change in height in a tape-shaped section of a functional element, with a passage 12 extending parallel to the tape surface in an overlapping part of the tape.

The lock element 4 in accordance with FIG. 5D, formed on a tape-shaped end of a first functional element, e.g. a retractor element 1, is suitable for holding a tape-shaped end of a further functional element, e.g. a further retractor element 1 or an extension element 5, as the closing element 3 thereof such that both functional elements extend in the same direction, e.g. for an extension of a retractor element 1 or for the direct connection of two retractor elements 1 extending toward one another, analogous to those in FIG. 2.

For this purpose, the lock element 4 features, at the end of a functional element, on a passage 12 extending parallel to the tape surface and in the direction of the tape. Alternatively, other angles between passage and tape are also possible here.

Alternatively, the passage 12 can be formed in a separate lock element 4 and have a passage height which permits the insertion and clamping of two closing elements 3 extending in parallel (FIG. 5E) or of several of such closing elements.

In the exemplary embodiment according to FIG. 6, the lock element is embodied e.g. as a separate part in such a way that it makes it possible to hold two closing elements 3, comparable with the embodiment in FIG. 5E. However, the illustrated embodiment renders possible the cross connection of individual functional elements. To this end, as illustrated in FIG. 6, the lock element 4 has a first passage 12 as holding option for a closing element 3 (not illustrated) and a second passage 12 as a holding option for a further closing element 3 (not illustrated), wherein the second passage 12 is arranged at an angle deviating from the first passage 12. FIG. 6 illustrates an orthogonal arrangement of the two passages 12 for closing elements 3 in an exemplary fashion. Deviating from this, the angle can be embodied in accordance with the requirements in the operation field and can lie between 0° and 180°.

FIGS. 7A and 7B illustrate alternative embodiments of closing elements 3, which, for example, can be arranged on an extension element 5 or a cross-connection element 6 or on other elements. The tape-shaped closing element 3 has at its end a planar thickening 15 of the tape, which corresponds to a slit 14 on the longitudinal axis of the tape. As a result of the slit 14, the closing element 3 can be forced into a lock element 4, in this case, for example, one in accordance with FIG. 6, until it snaps in behind the thickening 15. Connections of various functional elements are to be prepared and secured thus in order, when used, to be set easily and quickly to the appropriate length. The lock element 4 used in FIG. 7A realizes the connection with a further functional element along the tape longitudinal axis of the closing element 3, which carries the lock element 4, or perpendicular thereto.

The embodiment in accordance with FIG. 7B differs from the one in accordance with FIG. 7A by virtue of the lack of the slit and the addition of a further thickening 15, which is embodied in a mirror-image fashion and at such a distance from the first tape end that a lock element 4 forced over the first thickening 15 can only be displaced slightly on the tape, to be precise as far as the second thickening 15, and cannot, or only with great difficulties, be forced over the second thickening 15. This can also prepare connections between functional elements for later use; however, according to FIG. 7B, these are restricted to a defined position of the lock element 4. A lock element in accordance with FIG. 6 is also illustrated in FIG. 7B. Alternatively, use can also be made of other ones, formed separately or on a functional element.

FIG. 8 illustrates a functional element, e.g. a tape-shaped extension element 5, at the one end of which a closing element 3 and at the other end of which a lock element 4, e.g. in accordance with FIG. 3A is formed. In order to amplify the auto-clamping holding forces, the closing element 3 has microstructuring 17 on its surface. The latter is formed e.g. as texture, i.e. of regularly recurring geometric structures of the order of several tenths of millimeters. Alternatively, it is also possible to use irregular structures, which, for example, can be produced by means of blasting methods. Alternatively, or in addition thereto, microstructuring can also be formed on the contact face of a lock element 4, which is connected to the closing element 3 by force fit.

In a further exemplary embodiment, a retraction system according to the invention for use in the wrist region is, in an exemplary fashion, schematically illustrated in FIG. 9. The retraction system in accordance with FIG. 9 encompasses the body part, in this case a wrist, in a circular fashion in two separated positions and has a number of different functional elements for retracting and fixing the whole system.

Here, the system comprises a plate-shaped shape element 7, which is arranged on the opposite side of the region of the wrist to be opened up and adapts elastically to the partial circumference of the wrist. The retraction is brought about by four retractor elements 1, which can have different designs. Arranged at the end of the retractor elements 1, there are closing elements 3 in the form of tape-shaped ends, permitting a length setting required for encompassing the respective body section. On the other hand, the operator can moreover easily correct the length setting or adapt it in accordance with the course of the operation at any time.

The tape-shaped closing elements 3 of the two retractor elements 1 of the first retractor layer are respectively inserted into a lock element 4 of the shape element 7 and securely clamped by a clamping effect, as explained in relation to FIG. 4A. As a result, there is an auto-clamping, continuously adjustable retraction.

In addition to these two retractor elements 1, a cross-connection element 6 is also connected to the shape element 7, realizing a stable cross connection between the two retractor layers. Here, a tape-shaped closing element 3 of the cross-connection element 6 is held in a further lock element 4 of the shape element 7. This lock element 4 is arranged at right angles to the two above-described lock elements 4, and so the cross-connection element 6 is arranged along the wrist. At the other end of the cross-connection element 6, there is a connection to a retractor element 1 via a separate lock element 4 with an orthogonal holding option for the closing element 3 of the cross-connection element 6. Here the lock element 4 is embodied analogously to the one in FIG. 5.

The separate lock element 4 holds the tape of a retractor element 1 of the second retractor layer in the second plane, and so this retractor layer also lies at right angles to the cross-connection element 6. A further retractor element 1 belongs to the second retractor layer. The two retractor elements 1 of the second layer are connected to one another via a lock element 4 and a closing element 3, of which each is integrated into respectively one of the two retractor elements 1.

The retraction system furthermore comprises a specific, anatomical shape element 7 in the form of a finger attachment. This ring-like shape element 7 is plugged onto a finger and, in so doing, has a lock element 4 for holding a closing element 3 of a further retractor element 1 extending in the direction of the wrist.

Various functional elements, sections thereof, or else closing elements 3 can also have an elastic design in this embodiment. An elasticity, for example of the retractor elements 1, encompassing the wrist in a circular fashion and optionally also extending up to the finger, and of the shape element 7 allow the illustrated system to be adapted to various sizes and strengths of a wrist.

LIST OF REFERENCE SIGNS

1 Retractor element
3 Closing element
4 Lock element
5 Extension element
6 Cross-connection element
7 Shape element
8 Adaptation element
9 Web-like clamping element
10 Cutout
11 Thinned section
12 Passage
13 Compensation elements
14 Slit
15 Thickening
17 Microstructuring
18 External system
20 Bone
21 Tissue

The invention claimed is:

1. A modular retraction system, comprising:
    at least two first functional elements, each first functional element comprising:
        a flexible tape-shaped element; and
        a flexible hook-shaped retractor element disposed on a first end of the flexible tape-shaped element, wherein the flexible hook-shaped retractor element is embodied to be flexible such that, during a retraction, the flexible hook-shaped retractor element nestles against tissue to be retracted in an operation field, and wherein the flexible hook-shaped retractor element is integral with the flexible tape-shaped element;
    wherein at least one of the at least two first functional elements further comprises a closing element disposed on a second end of the flexible tape-shaped element opposite the first end; and
    at least one second functional element comprising a lock element, wherein the closing element is configured to be inserted into the lock element to selectively secure the at least one of the at least two first functional elements to the at least one second functional element in a desired relative position, and wherein the at least one second functional element is free of a hook-shaped retractor element.

2. The modular retraction system of claim 1, wherein each first functional element is one-piece.

3. The modular retraction system of claim 1, wherein each first functional element is free of a pivotal connection between the flexible tape-shaped element and the flexible hook-shaped retractor element.

4. The modular retraction system of claim 1, wherein the flexible tape-shaped element is a first flexible tape-shaped element, and wherein the at least one second functional element further comprises a second flexible tape-shaped element, wherein the lock element is disposed on one end of the second flexible tape-shaped element.

5. The modular retraction system of claim 1, wherein the at least one second functional element further comprises a specific shape element adapted to be applied to a specific body part, and wherein the lock element is disposed on the specific shape element.

6. The modular retraction system of claim 5, wherein the specific body part includes a finger, a limb, or a back.

7. The modular retraction system of claim 5, wherein the at least one second functional element comprises a partial cuff that is configured to wrap partially around the specific body part, wherein the at least one second functional element comprises a plurality of lock elements including a first subset positioned along a first edge of the partial cuff and a second subset positioned along a second edge of the partial cuff.

8. The modular retraction system of claim 1, wherein the tape-shaped element is a first tape-shaped element and the closing element is a first closing element, the retraction system further comprising:
    at least one third functional element comprising:
        a second tape-shaped element;
        a second closing element disposed on a first end of the second tape-shaped element; and
        a third closing element disposed on a second end of the second tape-shaped element opposite the first end of the second tape-shaped element;
    wherein the at least one third functional element is free of a hook-shaped retractor element.

9. The modular retraction system of claim 1, wherein the flexible hook-shaped retractor element is flexible enough to conform to tissue to be retracted while still holding down the tissue for retraction.

10. The modular retraction system of claim 1, wherein the at least two first functional elements and the at least one second functional element are constructed of a material that is transparent to x-rays.

11. The modular retraction system of claim 1, wherein the at least one second functional element includes a plurality of second functional elements for customization of the retraction system for retraction of a specific body part.

12. The modular retraction system of claim 1, wherein the at least one second functional element includes a lock element that is configured to receive more than one closing element.

13. The modular retraction system of claim 12, wherein the lock element that is configured to receive more than one closing element is configured to receive more than one longitudinally aligned closing element.

14. The modular retraction system of claim 12, wherein the lock element that is configured to receive more than one closing element is configured to receive two closing elements that are perpendicular to each other.

15. A modular retraction system for retracting tissue from around one or more bones of a limb, comprising:
    a plurality of first functional elements, wherein each first functional element is one-piece and comprises:
        a flexible tape-shaped portion that has a free end that defines a closing element; and
        a flexible hook-shaped retractor portion that defines an opposite end of the first functional element, wherein the flexible hook-shaped retractor portion is configured to be inserted under a bone of the one or more bones of the limb, and wherein the flexible hook-shaped retractor portion is embodied to be flexible such that, during a retraction, the flexible hook-shaped retractor portion nestles against tissue to be retracted in an operation field; and a second functional element comprising a partial cuff that is configured to wrap partially around the limb, wherein the second functional element comprises a plurality of lock elements including a first subset positioned along a first edge of the partial cuff and a second subset positioned along a second edge of the partial cuff, wherein the plurality of lock elements are each configured to receive and retain a respective closing element of a respective first functional element of the plurality of first functional elements.

16. The modular retraction system of claim 15, wherein the plurality of first functional elements and the second functional element are constructed of a material that is transparent to x-rays.

17. The modular retraction system of claim 15, wherein the flexible hook-shaped retractor portion has a generally S-shaped profile.

18. The modular retraction system of claim 15, wherein the modular retraction system has a retracted configuration when installed on the limb, wherein the limb has an exposed incision, wherein in the retracted configuration:
the partial cuff is positioned partially around the limb opposite the exposed incision;
the flexible hook-shaped retractor portion of a first functional element of the plurality of first functional elements is engaged with a bone of the one or more bones;
the flexible tape-shaped portion of the second first functional element of the plurality of first functional elements is retained by a lock element of the first subset;
the flexible hook-shaped retractor portion of a second first functional element of the plurality of first functional elements is engaged with a bone of the one or more bones; and
the flexible tape-shaped portion of the second first functional element of the plurality of first functional elements is retained by a lock element of the second subset.

19. The modular retraction system of claim 18, wherein in the retracted configuration the one or more bones are exposed via the exposed incision to define a retraction condition, wherein the modular retraction system is configured so that in the retracted configuration, the limb may be moved without disruption of the retraction condition.

20. The modular retraction system of claim 18, wherein in the retracted configuration, the flexible tape-shaped portions of the first and second first functional elements are nestled against the tissue.

21. A modular retraction system, comprising:
at least two first functional elements, each first functional element comprising:
a flexible tape-shaped element; and
a flexible hook-shaped retractor element disposed on a first end of the flexible tape-shaped element, wherein the flexible hook-shaped retractor element is embodied to be flexible such that, during a retraction, the flexible hook-shaped element nestles against tissue to be retracted in an operation field, and wherein the flexible hook-shaped retractor element is flexible enough to conform to tissue to be retracted while still holding down the tissue for retraction;
wherein at least one of the at least two first functional elements further comprises a closing element disposed on a second end of the flexible tape-shaped element opposite the first end; and at least one second functional element comprising a lock element, wherein the closing element is configured to be inserted into the lock element to selectively secure the at least one of the at least two first functional elements to the at least one second functional element in a desired relative position, and wherein the at least one second functional element is free of a hook-shaped retractor element.

22. The modular retraction system of claim 21, wherein each first functional element is one-piece.

23. The modular retraction system of claim 21, wherein the flexible hook-shaped retractor element is integral with the flexible tape-shaped element.

24. The modular retraction system of claim 21, wherein each first functional element is free of a pivotal connection between the flexible tape-shaped element and the flexible hook-shaped retractor element.

25. The modular retraction system of claim 21, wherein the flexible tape-shaped element is a first flexible tape-shaped element, and wherein the at least one second functional element further comprises a second flexible tape-shaped element, wherein the lock element is disposed on one end of the second flexible tape-shaped element.

26. The modular retraction system of claim 21, wherein the at least one second functional element further comprises a specific shape element adapted to be applied to a specific body part, and wherein the lock element is disposed on the specific shape element.

27. The modular retraction system of claim 26, wherein the specific body part includes a finger, a limb, or a back.

28. The modular retraction system of claim 26, wherein the at least one second functional element comprises a partial cuff that is configured to wrap partially around the specific body part, wherein the at least one second functional element comprises a plurality of lock elements including a first subset positioned along a first edge of the partial cuff and a second subset positioned along a second edge of the partial cuff.

29. The modular retraction system of claim 21, wherein the tape-shaped element is a first tape-shaped element and the closing element is a first closing element, the retraction system further comprising:
at least one third functional element comprising:
a second tape-shaped element;
a second closing element disposed on a first end of the second tape-shaped element; and
a third closing element disposed on a second end of the second tape-shaped element opposite the first end of the second tape-shaped element;
wherein the at least one third functional element is free of a hook-shaped retractor element.

30. The modular retraction system of claim 21, wherein the at least two first functional elements and the at least one second functional element are constructed of a material that is transparent to x-rays.

31. The modular retraction system of claim 21, wherein the at least one second functional element includes a plurality of second functional elements for customization of the retraction system for retraction of a specific body part.

32. The modular retraction system of claim 21, wherein the at least one second functional element includes a lock element that is configured to receive more than one closing element.

33. The modular retraction system of claim 32, wherein the lock element that is configured to receive more than one closing element is configured to receive more than one longitudinally aligned closing element.

34. The modular retraction system of claim 32, wherein the lock element that is configured to receive more than one closing element is configured to receive two closing elements that are perpendicular to each other.

* * * * *